United States Patent [19]

Wheeler

[11] 4,256,659

[45] Mar. 17, 1981

[54] METHOD OF PREPARING 2-ARYL-1,3-CYCLOHEXANEDIONE COMPOUNDS

[75] Inventor: Thomas N. Wheeler, Charleston, W. Va.

[73] Assignee: Union Carbide Corporation, New York, N.Y.

[21] Appl. No.: 114,384

[22] Filed: Jan. 22, 1980

Related U.S. Application Data

[62] Division of Ser. No. 781,985, Mar. 28, 1977, Pat. No. 4,209,532.

[51] Int. Cl.$^3$ .................. C07C 79/36; C07C 121/76; C07C 147/06
[52] U.S. Cl. .................. 260/465 D; 260/465 R; 260/465 E; 260/465 F; 260/465 G; 260/465 H; 568/29; 568/30; 568/31; 568/36; 568/42; 564/166; 564/169; 564/305; 564/441; 564/442; 564/443; 568/43; 568/306; 568/316; 564/153; 564/154; 564/156; 564/162

[58] Field of Search .......... 260/465 R, 465 D, 465 E, 260/465 F, 465 G, 465 H, 558 R, 558 S, 558 A, 558 D, 559 R, 559 A, 559 T, 570.8 R, 571, 576, 578; 568/29, 30, 31, 36, 42, 43, 316, 306

[56] References Cited

U.S. PATENT DOCUMENTS

| | | | |
|---|---|---|---|
| 3,273,992 | 9/1966 | Treves et al. | 71/2.3 |
| 3,801,630 | 4/1974 | Diehl et al. | 260/551 S |
| 3,820,975 | 6/1974 | Poye et al. | 71/98 |
| 3,852,359 | 12/1974 | Dunbar et al. | 260/590 |
| 3,954,998 | 5/1976 | Durden et al. | 424/331 |
| 4,041,049 | 8/1977 | Müller et al. | 260/343.5 |
| 4,153,719 | 5/1979 | Diana | 424/282 |

OTHER PUBLICATIONS

Durden, "Biocidal Activity of Indondiones-1,3 and Related Compounds".
Betts et al., J. Chem. Soc., 1961, pp. 333–345.

*Primary Examiner*—Dolph H. Torrence
*Attorney, Agent, or Firm*—Dale Lynn Carlson

[57] ABSTRACT

2-Aryl-1,3-cyclohexanedione compounds and their alkali metal and ammonium salts exhibit outstanding herbicidal, miticidal and mite ovicidal activity.

1 Claim, No Drawings

METHOD OF PREPARING 2-ARYL-1,3-CYCLOHEXANEDIONE COMPOUNDS

This application is a division of our prior U.S. application Ser. No. 781,985, filing date 3/28/77, now U.S. Pat. No. 4,209,532.

This invention relates to 2-aryl-1, 3-cyclo-hexanedione compounds and methods of preparing same. In another aspect of this invention is directed to miticidal, mite ovicidal, post-emergent herbicidal and pre-emergent herbicidal compositions comprising an acceptable carrier and a pesticidally effective amount of a compound of this invention, as well as, to methods of controlling mites and plant pests which comprises subjecting the mites, the eggs of mites and the plant pest to a pesticidally effective amount of a compound of this invention.

More particuarly, this invention relates to compounds of the formula:

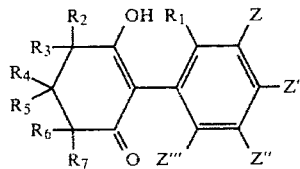

and alkali metal and ammonium salts thereof, wherein:

Z, Z', Z", Z'," are individually hydrogen, polyhaloalkyl, halogen, cyano, alkoxy, alkyl, nitro, alkylsulfonyl, alkylsulfinyl, alkylthio, haloalkyl, alkanoyl, amino or amido;

$R_1$ is alkyl, halogen, haloalkyl or polyhaloalkyl substituent;

$R_2$, $R_3$, $R_4$, $R_5$, $R_6$ and $R_7$ are individually hydrogen or either substituted or unsubstituted alkyl or phenyl wherein the permissible substituents are one or more alkyl, cyano, halogen, nitro, alkoxy, alkylthio, alkylsulfinyl, alkylsulfonyl, or dialkylamino substituents or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$ Z, Z' Z" and Z"' individually may not include more than ten aliphatic carbon atoms.

The following miticidally, mite ovicidally and herbicidally active compounds are illustrative of compounds within the purview of the generic formula set forth above, all of which can be conveniently prepared by the processes of this invention simply by selecting appropriate reactants for use in the procedures described below:

2-(2',4',6'-Trimethylphenyl)-1, 3-cyclohexanedione
2-(2'-Cyano-4',6'-dichlorophenyl)-1, 3-cyclohexanedione
2-(2'-Isopropyl-6'-cyanophenyl)-4, 6-dimethyl-1, 3- cyclohexanedione
2-(2'-Trifluoromethyl-6'-methyl)-4-trichloromethyl-1, 3-cyclohexandione
Triethylammonium salt of 2-(2',4'-dimethylphenyl)-5,5-dimethyl-1,3-cyclohexandione
Pyrrolidium salt of 2-(2', 4'-dichlorophenyl)-5,5-dimethyl-1,3-cyclohexanedione
Piperidinium salt of 2-(2',5'-dimethylphenyl)-5,5-dimethyl-1,3-cyclohexanedione
1-Adamantanammonium salt of 2-(2'-chlorophenyl)-5,5-dimethyl-1,3-cyclohexanedione
Pyridinium salt of 2-(2'-methylphenyl)-5,5-dimethyl-1,3-cyclohexanedione
Morpholinium salt of 2-(2',4'-dichlorphenyl)-5,5-dimethyl-1,3-cyclohexanedione
Benzyldimethylammonium salt of 2-(2', 4'-dimethylphenyl)-5,5-dimethyl-1,3-cyclohexanedione
Dicyclohexylammonium salt of 2-(2'-chlorophenyl)-5,5-dimethyl-1,3-cyclohexanedione
N,N-dimethylanilinium salt of 2-(2',4'-dimethylphenyl)-5,5-dimethyl-1,3-cyclohexanedione
2-Picolinium salt of 2-(2',4'-dichlorophenyl)-5,5-dimethyl-1,3-cyclohexanedione
Piperazinium salt of 2-(2',5'-dimethylphenyl)-5,5-dimethyl-1,3-cyclohexanedione
Imidazolium salt of 2-(2'- chlorophenyl)-5,5-dimethyl-1,3-cyclohexanedione
2-(2',4'-dimethylphenyl)-5-methyl-5-ethyl-1,3-cyclohexanedione
2-(2', 4'-dichlorphenyl)-5,5-diethyl-1,3-cyclohexanedione
2-(2'-methyl-4'-methoxyphenyl)-5-methyl-5-isobutyl-1,3-cyclohexanedione
2-(2'-methyl-4'-chlorophenyl)-5-methyl-5-isopropyl-1,3-cyclohexanedione
2-(2'-Ethyl-6'-ethoxy phenyl)-5,5-dimethyl-1, 3-cyclohexanedione
2-(2', 6'-Diethylphenyl)-5, 5-ditrifluoromethyl-1, 3-cyclohexanedione
2-(2'-Methyl-6'-(methylsulfinyl)phenyl)-5,5-dimethyl-1,3-cyclohexanedione
2-(2'-(Trichloromethyl-6'-cyanophenyl)-5,6-dimethyl-1,3-cyclohexanedione
2-(2',6'-Dimethyl-4'-t-butylphenyl)-5,5-dimethyl-1, 3-cyclohexanedione
3-(2', 4', 6'-Triethylphenyl)-spiro-[5,5]undecane-2,4-dione
Trimethylammonium salt of 2-(2'-ethyl-6'-ethoxy)-5,5-dimethyl-1,3-cyclohexandione
3(2'-Methylphenyl)-spiro [5,5] undecane-2, 4-dione
5- Phenyl-2(2', 4',6'-trimethylphenyl)-1, 3-cyclohexanedione
2-(2'-Methyl-4', 6'-dichlorophenyl)-5,5-dimethyl-1,3-cyclohexanedione
2(2'-Nitro-4',6'-Dibromophenyl)-5,5-dimethyl-1, 3-cyclohexanedione
5-(4'-Chlorophenyl)-2- (2',4',6'-trimethylphenyl)-1,3-cyclohexanedione
5-(3'-Bromophenyl)-2-(2',4',6'-trimethylphenyl)-1,3-cyclohexanedione
5-(2'-Methylthiophenyl)-2-(2',4',6'-trichlorophenyl)-1,3-cyclohexanedione
5-(4'-Methoxyphenyl)-2-(2',4',6'-trimethylphenyl)-1,3-cyclohexanedione
5-(3'-B-methoxyethylphenyl)-2-(2',4',6'-trimethylphenyl)-1,3-cyclohexanedione
2-(2',4',6'-Trimethylphenyl)-4-(4'-methylphenyl) -5,5-dimethyl-1,3-cyclohexanedione
2-(2',4',6'-Trimethylphenyl)-4-phenyl-5,5-dimethyl-1,3-cyclohexanedione
2-(2',4',6'-Trimethylphenyl)-4-(4'-chlorophenyl)-5,5-dimethyl-1,3-cyclohexanedione
2-(2',4',6'-Trimethylphenyl)-4-methoxy-5,5-dimethyl-1, 3-cyclohexanedione
2-(2',4',6'-Trimethylphenyl)-4, 5-dimethyl-1, 3-cyclohexanedione 2-(2',4',6'-Trimethylphenyl)-4-(4'-dimethylaminophenyl)-5-methyl-1,3-cyclohexanedione
5-(4'-Dimethylaminophenyl)-2-(2',6'-dimethylphenyl)-4-methyl-1, 3-cyclophexanedione
2-(2'-N-methylcarbamoyl-6'-methylphenyl)-4-(4'-methoxyphenyl)-5, 6-dimethyl-1, 3-cyclohexanedione
2-(2',6'-Dimethylphenyl)-4-(4'-methylthiophenyl)-5,5-dimethyl-1, 3-cyclohexanedione
2-(2'-Methyl-3',6'-dicyanophenyl)-6-(methylthioethyl)-1,3-cyclohexanedione
5-(4'-Methylsulfinylphenyl)-4,6-dimethyl-2-(2',6'-Dimethylphenyl)-1,3-cyclohexanedione
N-Methylpiperdinium salt of 5-(2'-Methoxyphenyl)2-(2',4',6'-trimethylphenyl)-1,3-cyclohexanedione
Trimethylammonium salt of 2-(2',6'-Dimethylphenyl)-4-(4'-methylthiophenyl)-5,6-dimethyl-1,3-cyclohexanedione
2(2'-Chloro-4'-methoxyphenyl)-5,5-dimethyl,-1,3-cyclohexanedione
2-(2'-Methyl-4'-cyanophenyl)-5,5-dimethyl-1,3-cyclohexanedione
2-(2'-Methyl-4'-trifluoromethylphenyl)-5,5-dimethyl-1,3-cyclohexanedione
2-(2'-Trifluoromethyl-4'-methoxyphenyl)-5,5-dimethyl-1,3-cyclohexanedione
2- (2'-Trifluoromethyl-4'-chlorophenyl)-5,5-dimethyl-1,3-cyclophexanedione
2-(2'-Trifluoromethyl-4'-cyanophenyl)-5,5-dimethyl-1,3-cyclohexanedione
2(2',4'-Dimethylphenyl)-5-phenyl-1,3-cyclohexanedione
2-(2'-Methylphenyl)-5-(2'-methylsulfonylmethyl)-1,3-cyclohexanedione
2-(2'-Methylphenyl)-5-(2'-chlorophenyl)-1,3-cyclohexanedione
2-(2'Methylphenyl)-5-(4'-nitrophenyl)-1,3-cyclohexanedione
2-(2'-Methylphenyl)-5-(4'-cyanophenyl)-1,3-cyclohexanedione
2-(2',4'-Dimethylphenyl)-5-(2'-methylphenyl)-1,3-cyclohexanedione
2-(2',4'-Dimethylphenyl)-4-(4'-trifluoromethylphenyl)-1,3-cyclohexanedione
2-(2',4'-Dimethylphenyl)-5-(2'-chlorophenyl)-1,3-cyclohexanedione
2-(2',4'-Dichlorophenyl)-6-(2'-methylthiophenyl)-1,3-cyclohexanedione
2-(2',4'-Dichlorophenyl)-5-(4'-methylphenyl)-1,3-cyclohexanedione
2-(2',4'-Dichlorophenyl)-5-(4'-methoxyphenyl)-1,3-cyclohexanedione
3-(2'-Methylphenyl)-spiro[5.5]undecane-2,4-dione
3-(2',4'-Dimethylphenyl)-spiro[5.5]undecane-2,4-dione
3-(2'-Chlorophenyl)-spiro[5.5]undecane-2,4-dione
3-(2',4'-Dichlorophenyl)-spiro[5.5]undecane-2,4-dione
2-(2',4'-Dimethylphenyl)-4,5-diethyl-1,3-cyclohexanedione
2-(2',4'-Difluorophenyl)-6-methyl-1,3-cyclohexanedione
2-(2'-methyl-5'-cyanophenyl)-6-methoxymethyl-1,3-cyclohexanedione
2(2',4'-Dibromophenyl)-4-(4'-methylthiophenyl)-5-methyl-1,3-cyclohexanedione
2-(2',4'-Dichlorophenyl)-6-(4'-dimethylaminophenyl)-1,3-cyclohexanedione
2-(2'-Trifluoromethyl-5-cyanophenyl)-6-methylsulfinylethyl-1,3-cyclohexanedione
2-(2'-chloro-4'-methoxyphenyl)-4,6-dimethyl-1,3-cyclohexanedione
The pyridinium salt of 2-(2',4'-Dibromophenyl)-6-methoxymethyl-1,3-cyclohexanedione
The N-methylmorpholinium salt of 2-(2'-methylphenyl)-4,6-diethyl-1,3-cyclohexanedione
5-(2',4'-Dimethylphenyl)-2-(2',4',6'- trichlorophenyl)-1,3-cyclohexanedione
5-(2',4'-Dichlorobutyl)-2-(2'-ethoxy-3',5',6'-trifluorophenyl)-1,3-cyclohexanedione
5-(Methylthiomethyl)-2-(2'-chloro-6'-cyanophenyl)-1,3-cyclohexanedione
5-(2'-Dimethylaminophenyl)-2-(2',6'-dimethylphenyl)-1,3-cyclohexanedione
2-(2'-Nitro-3'-methylthio-6'-trichloromethylphenyl)-5,5-dimethyl-1,3-cyclohexanedione
2-(2'-methyl-5'-cyano-6'-nitrophenyl)-4,6-dimethyl-1,3-cyclohexanedione
2-(2',4'-Dichloro-6'-trifluoromethylphenyl)-4-(2'-chloroethyl)-1,3-cyclohexanedione
3-(2'-Chloro-6'-fluorophenyl)-spiro[5,5]undecane-2,4-dione
2-(b 2'-Chloro-4'-nitro-6'-cyanophenyl)-5,5-propyl-1,3-cyclophexanedione
2-(2',6'-Dichloro-4'-nitrophenyl)-5-(2'-cyanoethyl)-1,3-cyclohexanedione
2-(2'-Chloro-6'-methoxy-4'-nitrophenyl)-5,5-dimethyl-1,3-cyclohexanedione
2-(2'-Chloro-6'-cyano-4'-nitrophenyl)-5,5-dimethyl-1,3-cyclohexanedione
2-(2'-Bromo-6'-methoxyphenyl)-1,3-cyclohexanedione
2-(2'-Methyl-6'-nitrophenyl) -1,3,-cyclohexanedione
2(2'-Trifluromethyl-6'-nitropenyl)-1,3-cyclohexanedione
2-(2',6'-Dichloro-4'-nitrophenyl)-1,3-cyclohexanedione
2-(2'-Chloro-6'-methoxy-4'-nitrophenyl)-1,3-cyclohexanedione
2-(2'-Chloro-6'-cyano-4'-nitrophenyl)-1,3-cyclohexanedione
2-(2'-Chloro-4',6'-dinitrophenyl)-1,3-cyclohexanedione
2-(2'-Methyl4',6'-dinitropheny)-1,3-cyclohexanedione
4-(4'-Chlorophenyl)-2,(2'-chloro-4'-nitrophenyl)-1,3-cyclohexanedione
5-(4'-Cyanophenyl)-2-(2'-chloro-6'-methoxy-4'-nitrophenyl)-1,3-cyclohexanedione
5-(2',4'-Dichlorophenyl)-2-(2',4'-dichloro-6'-nitrophenyl)-1,3-cyclohexanedione
5-(3'-Nitrophenyl)-2-(2'-chloro-4'-nitrophenyl)-1,3-cyclohexanedione
5-Phenyl-2-(2'-methyl-6'-chloro-4'-nitrophenyl)-1,3-cyclohexanedione
3-(2'-Chloro-6'-nitrophenyl)-spiro[5.5]undecane-2,4-dione
3-(2',6'-Dichloro-4'-nitrophenyl)-spiro[5.5]undecane-2,4-dione
2-(2'-Trifluoromethyl-4'-aminophenyl)-5,5-dimethyl-1,3-cyclohexanedione
2-(2',4'-Dichloro-6'-aminophenyl)-5,5-dimethyl-1,3-cyclohexanedione
2-(2',6'-Dichloro-4'-aminophenyl)-5,6-dimethyl-1,3-cyclohexanedione
2-(2'-Chloro-6'-nitro-4'-aminophenyl)-5,5-dimethyl-1,3-cyclohexanedione
5-(4'-Chlorophenyl)-2-(2'-chloro-6'-methoxy-4'-aminophenyl)-1,3-cyclohexanedione
5-(4'-Chloro-6'-nitrophenyl)-2-(2'-bromo-4'-methylsulfinyl-6'-cyanophenyl)1,3-cyclohexanedione 3-(2'-Chloro-6'-aminophenyl)-spiro [5.5] undecane-2,4-dione
2-(2',6'-Dichloro-4'-aminophenyl)-1,3-cyclohexanedione
2-(2'-Methyl-6'-nitrophenyl)-5-methoxymethyl-1,3-cyclohexanedione
2-(2'-Chloro-6'-nitrophenyl)-5,5-dimethyl-1,3-cyclohexanedione
2-(2'-Methyl-6'-nitrophenyl)-1,3-cyclohexanedione
2-(2'-Chloro-6'-nitrophenyl)-1,3-cyclohexanedione
2-(2'-Chloro-6'-methoxyphenyl)-5,6-dimethyl-1,3-cyclohexanedione
2-(2'-Chloro-6'-methoxyphenyl)-4,4-dimethyl-1,3-cyclohexanedione
2-(2'-Methyl-3'-nitro-6'-methoxyphenyl)-4,5-dimethyl-1,3-cyclohexanedione
2-(2'-Chloro-6'-methoxyphenyl)-1,3-cyclohexanedione
2-(2'-Methyl-4'-nitro-6'-methoxyphenyl)-1,3-cyclohexanedione
2-(2'-Bromo-4'-nitro-6'-idophenyl)-4,5-dimethyl-1,3-cyclohexanedione
2-(2'-Bromo-4'-aminophenyl)-5,5-dimethyl-1,3-cyclohexanedione
2-(2',6'-Dibromophenyl)-5,5-dimethyl-1,3-cyclohexanedione
2-(2'-Bromo-6'-aminophenyl)-1,3-cyclohexanedione
2-(2'-Bromo-5'-chloro-6'-fluorophenyl)-1,3-cyclohexanedione
2-(2',4'-Dichlorophenyl)-5,5-dimethyl-1,3-cyclohexanedione
2-(2',4-Dichloro-6'-tribromomethylphenyl)-1,3-cyclohexanedione
2-(2',4',6'-Trifluorophenyl)-5,5-dimeth6yl-1,3-cyclohexanedione
2-(2',4',6'-Tribromophenyl)-1,3-cyclohexanedione
3-(2'-Chloro-6'-bromophenyl)-spiro[5,5] undecane-2,4-dione
3-(2',4',6'-Trimethylphenyl)-spiro[5,5] undecane-2,4-dione
3-(2',4',6'-Trichlorophenyl)-spiro[5.5] undecane-2,4-dione
2-(2'-Methyl-6'-cyano-5'-nitrophenyl)-5,5-dimethyl-1,3-cyclohexanedione
2-(2'-Methyl-6'-cyano-4'-nitrophenyl)-1,3-cyclohexanedione
2-(2'-Chloro-6'-cyanophenyl)-1,3-cyclohexanedione
2-(2'-Chloro-4'-cyanophenyl)-6-trichloromethyl-1,3-cyclohexanedione
2-(2',6'-Dichloro-4'-cyanophenyl)-1, 3-cyclohexanedione
5-(2',4'-Dimethyloxyphenyl)-2-(2',6'-dimethylphenyl)-1,3-cyclohexanedione
5-(2'-Cyanopropyl)-6-methyl-2-(2',6'-dimethylphenyl)-1,3-cyclohexanedione
5-(3'-Ethylsulfinylphenyl)-2-(2',6-dichlorophenyl)-1,3-cyclohexanedione
3-(2',4'-Dimethylphenyl)-bicyclo [3.2.1] octane-2,4-dione
3-(2',4'-Dichlorophenyl)-bicyclo [4.4.0] decane-2,4-dione All compounds within the purview of the above generic formula exhibit miticidal, mita ovicidal, pre-emergent herbicidal and post-emergent herbicidal activity to a lesser or greater extent. Some of these compounds exhibit very high levels of miticidal, mite ovicidal or herbicidal activity in extremely small dosages while others require larger doses to be pesticidally effective. In general, the compounds of this invention that exhibit the highest order of herbicidal activity also exhibit the highest order of miticidal and mite ovicidal activity. Miticidal and mite ovicidal activity is greatest in those compounds having a hydrogen, alkyl, alkoxy, cyano, trihalomethyl or halogen substituent at one of the ortho positions of the 2-phenyl moiety and an alkyl or halogen substituent at the other ortho position of the 2-phenyl moiety. Especially active compounds are those in which the ortho substances are relatively small groups such as methoxy, ethoxy, methyl, ethyl, or halogen.

It has also been found that some of the pesticidal compositions of this invention exhibit excellent fumigant properties. In addition, these compounds are relatively non-toxic to mammals when used in amounts sufficient to kill mites, mite eggs or plant pest.

In addition to their utility as miticides, mite ovicides and herbicides, the compounds of this invention are also useful as intermediates in the preparation of other pesticidally active compounds. For example, 2-(2'-chloro-6'-methoxy-4'-nitrophenyl)-5,5-dimethyl-1,3-cyclohexanedione can be reacted with 2-ethylhexanoyl chloride in the presence of pyridine as solvent and acid acceptor to form 3-(2-ethylhexanoyloxy)-2-(2'-chloro-6'-methoxy-4'-nitrophenyl)-5,5-dimethyl-2-cyclohexenone, the corresponding pesticidally active enol ester compound. The 2-aryl-1, 3-cyclohexanedione compounds of this invention can also be reacted with other chemical species containing electron deficient reaction sites as for example organic anhydride compounds such as acetic anhydride. Certain reactions leading to the pesticidally active enol ester derivatives are described in more detail in my copending U.S. Pat. Application Ser. No. 781,781 entitled "BIOCIDAL 2-ARYL-1, 3-CYCLOHEXANEDIONE ENOL ESTER COMPOUNDS", filed 3/28/77, abandoned.

Preferred because of their higher levels of miticidal, mite ovicidal and herbicidal activity and because of their utility as intermediates in the preparation of other pesticidally active compounds are the compounds of this invention in which, Z, Z' and Z" are individually alkyl, hydrogen, cyano, alkoxy, halogen or trihalomethyl;

$R_1$ is alkyl, or halogen;

$R_2$, $R_3$, $R_4$, $R_5$, $R_6$ and $R_7$ are individually hydrogen or alkyl.

The most active and particularly preferred compounds are those in which,

Z, Z', Z" and Z"' are individually hydrogen, methyl, methoxy, cyano or halogen;

$R_1$ is methyl or halogen;

$R_2$, $R_3$, $R_4$, $R_5$, $R_6$ and $R_7$ are individually hydrogen, methyl or ethyl;

The 2-aryl-1, 3-cyclohexanedione compounds of this invention can be conveniently prepared by a variety of methods. Two preferred methods for preparing the compounds of this invention are illustrated by the reaction schemes set below in which $R_1$, $R_2$, $R_3$, $R_4$, $R_5$, $R_6$, $R_7$, Z, Z', Z" and Z"' are as described above and $R_8$ is alkyl except as noted:

METHOD I

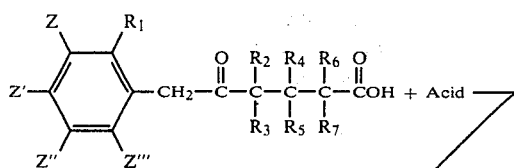

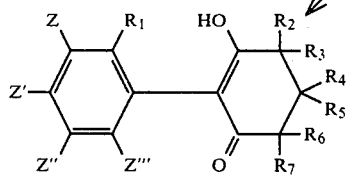

METHOD II

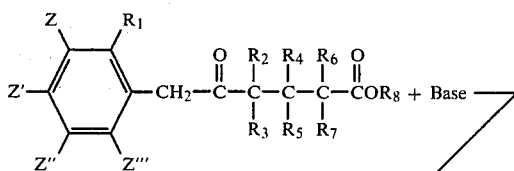

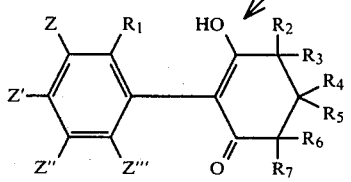

Preferably, the reactions illustrated in METHODS I and II are carried out by contacting equivalent amounts of the reactants in a suitable solvent. In the conduct of the reaction of METHOD II, types and quantities of the solvent employed are not critical. Illustrative of suitable inert solvents are ethanol, methanol, dimethylformamide, dimethylsulfoxide, methylene chloride, benzene, xylene, toluene, dioxane, dimethoxyethane, tetrahydrofuran and the like.

The reaction illustrated in METHOD I can be conducted in any solvent that is chemically inert to the reactants and to the reaction conditions, and in which the acid catalyst is soluble. Illustrative of such solvents are water and carboxylic acids, such as acetic acid, butanoic acid, or the like. The preferred reaction solvents are water and acetic acid.

The cyclization reaction illustrated in METHOD I is conducted in the presence of a strong mineral acid catalyst. Illustrative of mineral acids that are useful in the conduct of this reaction are sulfuric acid, hydrochloric acid, perchloric acid and the like. The preferred acid catalyst is sulfuric acid.

The quantity of acid catalyst employed in the conduct of the reaction of METHOD I is not critical. In general, to achieve a reasonable rate of reaction, the reaction is conducted in the presence of from about 1 to about 85 weight percent of the acid catalyst based on the total weight of the reaction solvent. Preferred acid concentrations are from about 50 to about 85 weight percent based on the weight of the reaction solvent.

The cyclization reaction illustrated in METHOD II is conducted in the presence of at least one equivalent of either a strong organic or a strong inorganic base. Illustrative of bases that are useful in the conduct of this reaction are the alkali metal alkoxides, as for example, sodium methoxide, sodium ethoxide or potassium tert-butoxide; the alkali metal alkylides; or the alkali metal hydrides such as sodium hydride, lithium hydride or the like. The preferred base in the conduct of this reaction is sodium hydride.

The reaction pressure and temperature at which the reactions of METHOD'S I and II are conducted are not critical. For convenience, these reactions are usually conducted at atmospheric or autogeneous pressure. In general, these reactions can be conducted at a temperature in the range of from about $-30°$ C. and upwards to approximately 200° C. and higher. Preferred reaction temperatures are from about 60° to about 120° C.

Alternative procedures for preparing a more limited class of 2-aryl-1, 3-cyclohexanedione compounds are illustrated by the general reaction schemes set forth below in which $R_1$, $R_2$, $R_3$, $R_4$, $R_5$, $R_6$, $R_7$, Z, Z', Z'' and Z''' are as described above and X is fluorine or chlorine except as noted:

METHOD III

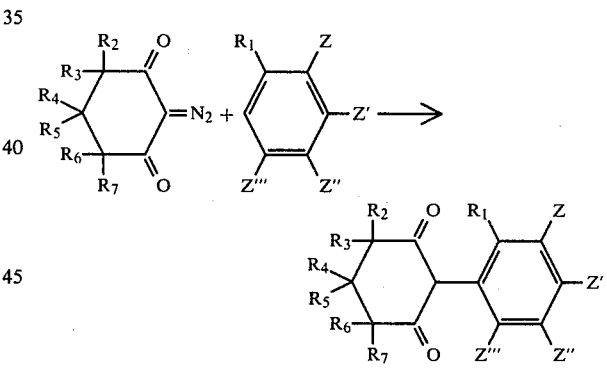

In METHOD III, $R_1$ is alkyl and Z, Z', Z'' and Z''' are other than nitro.

METHOD IV

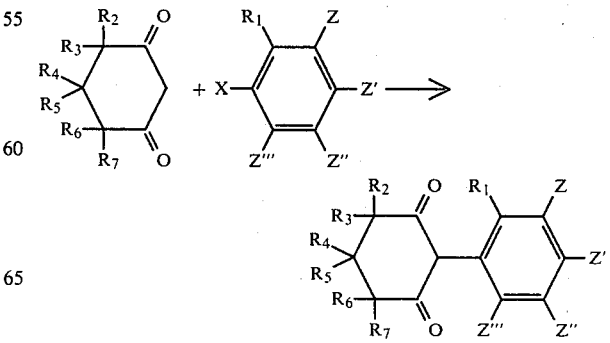

In Method IV, Z' is alkylsulfonyl or nitro; or Z' may also be alkyl or alkoxy when either $R_1$ or Z''' is nitro.

The procedure illustrated in METHOD III involves the photosensitized decomposition of a 2-diazocycloalkane-1, 3-dione compound in an aromatic solvent, in the presence of a photosensitizer, preferably benzophenone. In this procedure an appropriately substituted 2-diazocycloalkane-1, 3-dione compound is photochemically decomposed to form the corresponding triplet carbene which, in turn, reacts with a suitable aromatic solvent to form the desired 2-arylcycloalkane-1, 3-dione compound. The photolysis reaction is carried out using ultraviolet radiation having a wavelength of greater than 290 nanometers. The ultraviolet radiation can be obtained from any conventional ultraviolet radiation source known to those skilled in the photolysis art. Illustrative of suitable sources for generating ultraviolet radiation are high and low pressure mercury arc lamps, germacidal lamps, "black" lights and the like.

Preferably the reaction illustrated in METHOD IV is carried out by contacting equivalent amounts of the reactants in an appropriate solvent, in the presence of at least an equivalent of either an organic or an inorganic base. Illustrative of suitable reaction solvents, are dimethylformamide, dimethylsulfoxide, hexamethylphosphoramide and the like. Illustrative of bases that may be utilized in the conduct of this reaction are alkali metal carbonates or bicarbonates, as for example, sodium bicarbonate or potassium carbonate; alkali metal hydrides, such as lithium hydride, sodium hydride or potassium hydride, or alkali metal alkoxides or hydroxides, such as sodium hydroxide, sodium methoxide or potassium tert-butoxide. The preferred base is anhydrous potassium carbonate.

The reactions of METHODS III and IV are neither temperature nor pressure sensitive and may be conducted over a broad temperature and pressure range to yield the desired product. In general, these reactions can be conducted at a temperature of from about $-30°$ C. to about 200° C. For convenience these reactions are conducted at autogeneous or atmospheric pressure.

The alkali metal and ammonium salts of the compounds of this invention can be conveniently prepared in accordance with conventional methods. For example, the alkali metal and ammonium salts can be prepared by treating the corresponding 2-aryl-1, 3-cyclohexanedione compound with an alkali metal alkoxide, or ammonia, or an amine respectively.

The 6-aryl-5-ketopolyalkylhexanoic acid compounds utilized as reactants in the reaction illustrated in METHOD I can be conveniently prepared by reacting an appropriately polysubstituted benzyl cyanide compound with a suitable polyalkyl glutaric acid derivative in the presence of base to form the corresponding 6-aryl-6-cyano-5-ketopolyalkylhexanoic acid ester compound which, in turn, is hydrolyzed under acidic conditions to the desired reactant.

The 6-aryl-5-ketopolyalkylhexanoic acid ester compounds utilized as reactants in the reaction illustrated in METHOD II can be conveniently prepared by esterifying the 6-aryl-5-ketopolyalkylhexanoic acid reactant of METHOD I via conventional esterification techniques.

The 2-diazo-1, 3-cyclohexanedione compounds utilized as reactants in the reaction of Method III can be prepared by treating an appropriately substituted cyclohexanedione-1, 3-dione compound with a sulfonyl azide in the presence of an acid acceptor, as for example, a trialkylamine, as described in more detail in H. Stetter and K. Kiehr, *Chem. Ber.*, 98 1181 (1965), M. Regitz and P. Stodler, *Liebigs Ann. Chem.*, 687, 214 (1967) and reference cited therein. The cyclohexane-1, 3-dione compound, in turn, can be prepared by conventional methods, as for example by condensing an appropriately substituted α-β-unsaturated ketone with diethyl malonate in the presence of a base catalyst as described in more detail in K. W. Rosenmund, H. Herzberg and H. Scutt, *Chem. Ber.*, 87, 1258 (1954), C. K. Shuang and Y. L. Tien, *Chem. Ber.*, 69,27 (1936) and references cited therein.

The substituted aryl and cyclohexanedione compounds employed as reactants in the reaction illustrated in METHOD IV are known classes of compounds that can be either obtained from commercial sources or prepared in accordance with conventional methods known to those skilled in the synthetic arts.

The following specific examples are presented to more particularly illustrate the novel process of this invention and its use in preparing the novel compounds of this invention.

EXAMPLE I

Preparation of
2-(2'-Chloro-4'-nitrophenyl)-5,5-dimethyl-1,3-cyclohexanedione

A solution containing 42.05 g (0.300 mol) of 5,5-dimethyl-1,3-cyclohexanedione and 100 g (0.178 g-atom) of anhydrous potassium carbonate in 300 ml of dry dimethylformamide was heated to 75° C. under nitrogen and stirred for one hour. The 3, 4-dichloronitrobenzene, 57.60 g (0.300 mol) was dissolved in 100 ml dimethylformamide and added dropwise to the reaction mixture while stirring and maintaining the temperature of the reaction mixture at 75° C. A deep red-colored solution formed, and when the addition was complete the reaction temperature was raised to 100° C. and held at this temperature for 3 hours. Most of the dimethylformamide was removed by vacuum distillation. The residue was poured into 2l of ice water and extracted three times with 500 ml of benzene. Nitrogen was then passed through the aqueous solution while warming to remove dissolved benzene. The aqueous solution was cooled in an ice bath and acidified to give a tacky precipitate, which, upon warming solidified and was collected by suction filtration. The product was recrystallized from acetone to give 31.7 g (36%) of 2-(2'-Chloro-4'-nitrophenyl)-5,5-dimethyl-1, 3-cyclohexanedione as a white powder, m.p. 250°–253° C.

Calculated for $C_{14}H_{14}ClNO_4.1/2H_2O$: C, 55.18; H, 4.96; N, 4.60 Found: C, 55.53; H, 4.73; N, 5.09

EXAMPLE II

Preparation of
2-(2'-Chloro-4'-aminophenyl)-5,5-dimethyl-1, 3-cyclohexanedione

A solution of 20.0 g (0.067 mol) of 2-(2'-chloro-4'-nitrophenyl)-5,5-dimethyl-1,3-cyclohexanedione in 150 ml of concentrated ammonium hydroxide and 150 ml of ethanol was stirred at room temperature while passing hydrogen sulfide gas through the solution at such a rate that all of the $H_2S$ was absorbed. When the solution was saturated with $H_2S$, the temperature was raised to the reflux point and $H_2S$ continuously passed slowly through the refluxing solution for 24 hours. The reaction mixture was filtered to remove sulfur, and the filtrate evaporated under reduced pressure. To the residue was added 300 ml of 0.25N NaOH, and the solution filtered once more. The filtrate was cooled and carefully acidified to pH-4 with 6N HCl. 2-(2'-Chloro-4'-aminophenyl)-5,5-dimethyl-1, 3-cyclohexanedione was collected by suction filtration.

Yield: 13.3 g (74%), m.p. 218°–219° C. Calculated for: $C_{14}H_{16}Cl\ NO_2.1/2\ H_2O$. C, 61.20; H, 6.24; N, 5.10 Found; C, 60.44; H, 5.83; N, 5.32

EXAMPLE III

Preparation of 2-(2'-Chlorophenyl)-5,5-dimethyl-1, 3-cyclohexanedione 2-(2'-Chloro-4'-aminophenyl)-5,5-dimethyl-1, 3-cyclohexanedione (9.66 g. 0.0364 mol) was added to 7.0 ml of water, and mixture stirred and heated almost to boiling. An additional 15.0 ml of HCl was added and the mixture cooled to 0°–5° C. A solution of 3.22 g (0.0467 mol) of sodium nitrite in 9.0 ml of water was added dropwise while the reaction mixture was stirred and maintained at 0°–5° C. When the addition of the sodium nitrite solution was complete, the reaction mixture was stirred at 0°–5° C. for one hour.

The diazonium salt solution prepared above was added in portions to 161 ml of 50% hypophosphorous acid at 0° C., with stirring and cooling. The reaction mixture was stirred for 12 hours and filtered to give 8.55 g of a tan solid. This material was chromatographed through 250 g of silica gel (0.063–0.2 mm) eluting with a gradient from pure benzene to 70:30 benzene-ethyl acetate. A total of 7.12 g of reaction product was obtained from the chromatography and recrystallized from benzene-ethyl acetate to give 6.85 g (75%) of 2-(2'-chorophenyl)-5,5-dimethyl-1, 3-cyclohexanedione as white crystals, m.p. 191°–192° C.

Calculated for $C_{14}H_{15}C_1O_2$: C, 67.07; H, 6.03 Found: C, 67.04; H, 6.00.

EXAMPLE IV

Preparation of 2-(2', 4'-Dichlorophenyl)-5,5-dimethyl-1,3-cyclohexanedione

A fresh sample of cuprous chloride was prepared by slowly adding a solution of 2.09g of sodium bisulfite and 1.38 g of NaOH in 20 ml of water to a solution of 9.86 g $CuSO_4.5H_2O$ and 2.75 g NaCl in 100 ml of hot water. The suspension of CuCl was cooled to room temperaure, and washed several times with water while exercising care to avoid exposure of the cuprous chloride to air.

A suspension of 5.00 g (0.0188 mol) of 2-(2'-chloro-4'-aminophenyl)-5,5-dimethyl-1, 3 -cyclohexanedione in 75 ml of water containing 4.0 ml of concentrated HCl was stirred and heated almost to boiling for 10 min., then cooled to 10° C. and an additional 7 ml of conc. HCl added and the solution cooled to 0°–5° C. A solution of 2.00 g (0.0282 mol) of sodium nitrite in 6.0 ml of water was added dropwise to the amine hydrochloride solution while maintaining the temperature at 0°–5° C. When all the $NaNO_2$ solution had been added, the diazonium salt solution was stirred for 30 min. at 0° C.

The diazonium salt solution was added, in small portions to a solution of the cuprous chloride in 40 ml of conc. HCl at 0° C. When all of the diazonium salt solution had been added, the reaction mixture was stirred overnight at room temperatures and filtered to give 6.22 g of a tan solid, m.p. 175°–178° C. This crude product was chromatograhed through silica gel (0.063–0.2mm) using a benzene-ethyl acetate gradient from pure benzene to 70:30 benzene-ethyl acetate to give 3.51 g (65%) of 2-(2', 4'-Dichlorophenyl)-5,5-dimethyl-1, 3-cyclohexanedione as a white, crystalline solid, m.p. 208.5°–210° C.

Calculated for: $C_{14}H_{14}Cl_2O_2$: C, 58.97; H, 4.95 Found: C, 59.06; H, 4.82

EXAMPLE V

Preparation of 2-(2', 6'-Dichloro-4'-nitrophenyl)-5,5-dimethyl-1,3-cyclohexanedione A solution of 30.98 g (0.221 mol) of 5,5-dimethyl-1,3-cyclohexanedione and 76.36 g (0.553 mol) of anhydrous potassium carbonate in 300 ml of dimethylformamide was heated to 75° C. with stirring under $N_2$ for one hour. The 3,4,5-trichloronitrobenzene (50.0 g, 0.221 mol) was dissolved in 100 ml of dimethylformamide and added to the reaction mixture, while stirring and maintaining the temperature at 75° C. A deep red-colored solution was formed and when the addition was complete the temperature was raised to 100° C. and the mixture stirred over night at this temperature. Most of the dimethylformamide was removed by vacuum distillation, and 21 of water was added to the residue. The aqueous solution was extracted three times with 500 ml portions of benzene, then $N_2$ was passed through the aqueous solution while warming to remove dissolved benzene. The solution was cooled in an ice bath and acidified with 6N HCl to give 63.8g (87%) of 2-(2', 6'-dichloro-4'-nitrophenyl)-5,5-dimethyl-1,3-cyclohexanedione as a tan powder, m.p. 288°–290° C.

Calculated for $C_{14}H_{13}Cl_2NO_4$: C,50.93; H,3.97; N, 4.24 Found: C, 50.09; H, 3.79; N, 4.26

EXAMPLE VI

Preparation of 2-(2', 6'-Dichloro-4'-aminophenyl)-5,5-dimethyl-1,3-cyclohexanedione A solution of 20.0 g (0.0606 mol) of 2-(2', 6'-dichloro-4'-nitrophenyl)-5,5-dimethyl-1,3-cyclohexanedione in 150 ml conc. $NH_4OH$ and 150 ml of ethanol was stirred at room temperature while passing $H_2S$ gas through the solution at such a rate that all of the $H_2S$ was absorbed. After the solution was saturated with $H_2S$, it was refluxed 24 hours while continuously passing $H_2S$ slowly through the solution. The reaction mixture was cooled to room temperature, the precipitated sulfur removed by filtration, and the filtrate evaporated to dryness under reduced pressure. To the residue was added 300 ml of 0.25N NaOH, and the solution filtered once more. The filtrate was cooled and acidified to pH-4-with 6N HCl. A tan solid formed which was collected by filtration to give 11.2 g when dry. This material was washed with methylene chloride to give 8.2 g (45%) of 2-(2', 6'-dichloro-4"-aminophenyl)-5,5-dimethyl-1, 3-cyclohexanedione as a white powder, m.p. 243°d.

Calculated for $C_{14}H_{15}C_{12}NO_2$: C,56.02; H,5.04; N,4.67 Found: C,56.34; H, 4.95; N,4,67.

EXAMPLE VII

Preparation of 2-(2', 6'-Dichlorophenyl)-5,5-dimethyl-1,3-cyclohexanedione

The 2-(2', 6'-dichloro-4'-aminophenyl)-5,5-dimethyl-1,3-cyclohexanedione (5.00 g, 0.0167 mol) was added to 3.5 ml of concentrated HCl in 75 ml of water, and the mixture stirred and heated almost to boiling. The suspension was cooled to 10° C. and an additional 7.5 ml of conc. HCl was added. The mixture was cooled to 0°–5° C. and a solution of 1.44g (0.0209 mol) of sodium nitrite in 3.5 ml. of water was added dropwise while the reaction mixture was stirred and maintained at 0°–5° C. When addition of the sodium nitride solution was complete, the reaction mixture was stirred at 0° C. for one hour.

The diazonium salt solution prepared above was added in portions to 75 ml of 50% hypophosphorous acid at 0° C. with stirring and cooling. The reaction mixture was stirred for 2 hours and filtered to give 5.03 g of brown powder. This material was recrystallized from benzenechloroform to give 2.69 g of a light tan solid m.p. 227°–229° C. The residue from the mother liquor (1.70g) was chromatographed through silica gel (0.063–0.2mm) to give 0.84 g of a white solid, m.p. 228°–232° C. Total yield of 2-(2', 6'-Dichlorophenyl)-5,5-dimethyl-1,3-cyclohexane-1,3-dione was 3.53g (74%).

Calculated for: $C_{14}H_{14}Cl_2O_2$: C, 58.97; H, 4.95 Found: C, 58.64 H, 4.86

EXAMPLE VIII

Preparation of 2-(2', 4', 6'-Trimethylphenyl)-cyclohexane-1,3-dione

A solution of 5.00 g (0.036 mol) of 2-diazocyclohexane-1,3-dione in 500 ml of mesitylene (dry, distilled) containing 32.8 g (0.18 mol) benzophenone was degassed with nitrogen for one hour and irradiated with a 200 watt mercury arc lamp fitted with a borosilicte glass filter until the complete disappearance of the diazo band (4.68 u) in the infrared was observed. The reaction was also monitored by thin layer chromatography (90:10 ethyl acetate-benzene) and irradiation continued until no diazoketone at $R_f = 0.31$ could be seen. The irradiation required 11 hours. The mestylene was extracted with 0.25N sodium hydroxide until a small aliquot showed no cloudiness upon acidification. The combined base extracts were washed twice with 200 ml portions of ether, and acidified (pH 3–5) with 1N HCl. The aqueous solution was extracted three times with 75 ml portions of chloroform, dried over anhydrous $MgSO_4$, and the solvent stripped to give 5.06 g of a tan solid.

This solid was chromatographed through 250 g silica gel (0.063–0.2mm) eluting with a gradient from pure benzene to 80:20 benzene-ethyl acetate. A total of 2.60 g (31%) of a white solid (homogeneous by thin layer chromatography) was obtained and recrystallized from diisopropyl ether to give 1.96 g of 2-(2', 4', 6'-Trimethylphenyl)-cyclohexane-1,3-dione as white crystals, mp 196°–198° C.

Calculated for: $C_{15}H_{18}O_2$: C, 78.23; H, 7.88 Found: C, 77.94 H, 8.20

EXAMPLES IX AND X

Preparation of 2-(2', 4'-Dimethylphenyl)-5,5-dimethylcyclohexane-1,3-dione and 2-(2', 6'-dimethylphenyl)-5,5-dimethylcyclohexane-1,3-dione A solution of 5.00 g (0.0301 mol.) of 2-diazo-5,5-dimethylcyclohexane-1, 3-dione in 500 ml of a m-xylene containing 27.4 g (0.15 mol) of benzeophenone was degassed with nitrogen for one hour and irradiated overnight with a 200 watt mercury arc lamp fitted with a borosilicate glass filter. The photolysis mixture was extracted with 0.25N NaOH, the combined base extracts washed with ether and acidified with chloroform, dried over anhydrous $mgSO_4$ and the solvent removed to leave 3.61 g of a tan solid. Irradiation was repeated using 7.00 g (0.042 mol) of 2-diazo-5,5-dimethylcyclohexane-1, 3-dione and 38.38 g (0.21 mol) of benzophenone in 500 ml of m-xylene. Workup gave 5.48 g of tan solid.

The combined crude products (9.09 g) were chromatographed through silica gel (0.063–02. mm) using benzene-ethyl acetate as eluent. The column was eluted with (1) 500 ml benzene (2) ml of 95.5 benzene-ethyle acetate (3) 1000 ml of 90:10 benzene-ethyl acetate and (4) 1000 ml of 80:20 benzene-ethyl acetate. After collecting 2 liters of solvent, the column was attached to an automatic fraction collector and 15 ml fractions collected. Tubes 1–94 contained small amounts of a yellow oil. Tubes 95–150 contained a light yellow solid which showed one component ($R_f$ 0.55 in 50:50 hexane-ethyl acetate) by thin layer chromatography and weighed 2.18 g. This material was recrystallized from benzene to give 1.17 g of 2-(2', 4'-Dimethylphenyl)-5,5-dimethyl-1,3-cyclohexanedione as a white powder, mp 167°–169° C.

Calculated for: $C_{16}H_{20}O_2$: C, 78.65; H, 8.25 Found: C, 78.68; H, 8.12

This compound was shown to be 2-(2', 4'-dimethylphenyl)-5,5- dimethyl-1, 3-cyclohexandione.

Tubes 151–230 were combined to give 2.0 g of white solid showing one component ($R_f$ 0.57 in 50:50 hexane-ethyl acetate by thin layer chromatography. This material was recrystallized from benzene to give 1.90 g of 2-(2', 6'-Dimethylphenyl)-5,5-dimethyl-1, 3-cyclohexanedione as white crystals, mp 177°–186° C.

Calculated for: $C_{16}H_{20}O_2$: C, 78.65; H, 8.25 Found: C, 78.28; H, 8.21

This compound was shown to be 2-(2', 6'-Dimethylphenyl-5,5-dimethyl-1,3-cyclohexanedione.

EXAMPLE XI

Preparation of 2-Diazo-5-phenylcyclohexane-1,3-dione

A solution of 20.0 g (0.106mol) of 5-phenyl-cyclohexane-1,3-dione in 75 ml of ethanol was cooled to −10° C. and stirred magnetically under nitrogen. To the mixture was added 10.75 g (0.106 mol) of triethylamine. The tosyl azide (20.95 g 0.106 mol) was added all at once, and the mixture stirred for one hour at 0°–5° C. The solvent was removed under vacuum at a temperature less than 40° C. To the residue was added 200 ml ether, and the mixture extracted with a solution containing 3.1 g potassium hydroxide in 200 ml of water. The etheral solution was dried over anhydrous $MgSO_4$ filtered and the solvent removed to give a yellow solid which was recrystallized from ethanol -hexane to give 8.38 g (32%) of 2-diazo-5-phenyl-cyclohexane-1,3-dione as yellow crystals, mp 122°–124° C.

EXAMPLE XII

Preparation of 2-(2', 4', 6'-Trimethylphenyl)-5-phenylcyclohexane-1, 3-dione

A solution of 7.0 g (0.0327 mol) of 2-diazo-5-phenyl-cyclohexane-1, 3-dione and 29.77 g (0.163 mol) of benzophenone in 500 ml of mesitylene was degassed for one hour with nitrogen and irradiated with a 200 watt mercury arc lamp fitted with a borosilicate glass filter overnight. The photolysis mixture was extracted with 0.25 N sodium hydroxide, the combined base extracts washed with ether, acidified with 1N HCl, and extracted with chloroform. The chloroform solution was dried over anhydrous MgSO$_4$, and the solvent stripped to give 5.7 g of tan solid. This material was purified by column chromatography on silica gel (0.063–0.2mm) using benzene-ethyl acetate to give 5.7 g (57%) of a white solid. This was recrystallized from benzene-ethyl acetate to give 4.08 g (41%) of 2-(2', 4', 6'-Trimethylphenyl)-5-phenylcyclohexane-1, 3-dione as a white crystalline solid, mp. 215°–216° C.

Calculated for: C$_{21}$H$_{22}$O$_2$: C, 82.32; H, 7.24 Found: C, 82.38; H, 7.14

EXAMPLE XIII

Preparation of 2-(2', 6'-Dimethyl-4'-t-butylphenyl)-5,5-dimethyl-1,3-cyclohexanedione A solution of 7.00 g (0.042 mol) of 2diazo-5,5-dimethylcyclohexane-1,3-dione in 300 ml of 5-t-butyl-m-xylene and 250 ml chlorobenzene containing 38.38 g (0.21 mol) of benzophenone was irradiated overnight with a 200 watt mercury arc lamp fitted with a borosilicate glass filter after degassing for 1 hour under nitrogen. The photolysis mixture was extracted with 0.25 N NaOH, washed with either, acidified with 1N, HCl, and extracted with chloroform. The chloroform was dried over anhydrous MgSO$_4$ and stripped to give a crude yellow solid. The photolysis was repeated and the combined crude product from these reactions was chromatographed through silica gel (0.063–0.2 mm) using benzene-ethyl acetate. The solid obtained from the chromatography was recrystallized from benzene to give 2.76 g (11%) of 2-2', 6'-dimethyl-4'-butylphenyl)-5,5-dimethyl-1 3-cyclohexanedione as white crystals, mp 244°–49° C.

Calculated for: C$_{20}$H$_{28}$O$_2$: C, 79.95; H, 9.39 Found: C, 79.76; H, 9.45

EXAMPLE XIV

Preparation of 2-Diazodecalin-1,3-dione

A solution of 10.0 g (0.0768 mol) of decalin-1,3-dione in 50 ml of ethanol was magnetically stirred under nitrogen and cooled to −10° C. To the solution was added 7.77 g (0.0768 mol) of triethylamine followed by 15.14 g (0.0768 mol) of p-toluenesulfonylazide added all at once. The mixture was stirred for one hour at 0° C, and the solvent removed at reduced pressure at a temperature of less than 40° C. To the residue was added 200 ml of ether, and the ether removed to yield a yellow solid. This was recrystallized from ethanol to give 5.23 g of yellow crystals, mp 81°–83° C.

EXAMPLE XV

Preparation of 2-(2'-Methylphenyl)-decalin-1, 3-dione

A solution of 7.0 g (0.0364 mol) of 2-diazodecaline-1, 3-dione and 33.18 g (0.182 mol) of benzophenone in 500 ml of toluene was degassed for one hour with nitrogen and irradiated with a 200 watt mercury arc lamp fitted with a borosilicate glass filter overnight. The photolysis mixture was extracted with 0.25N NaOH, the combined base extracts washed with ether, acidified with 1M HCl and extracted with chloroform. The chloroform extracts were dried over anhydrous MgSO$_4$, and the solvent removed to give 4.56 g of a yellow crude product. This was purified by column chromatography through silica gel(0.063–0.2 mm) with benzene-ethyl acetate. The solid obtained was recrystallized from benzene to give 1.85 g (20%) of 2-(2'-Methylphenyl)- decalin-1, 3-dione as white crystals, mp 165°–167° C.

Calculated for: C$_{17}$H$_{20}$O$_2$: C, 79.65; H, 7.86 Found: C, 79.82; H, 7.43

EXAMPLE XVI

Preparation of Ethyl 6-(2',4'-Dimethylphenyl)-6-cyano-5-keto- 3, 3-dimethylhexanoate A clean, dry 500 ml 3-neck flask was equipped with a reflux condenser, mechanical stirrer, addition funnel and nitrogen inlet. The flask was charged with 70 ml of absolute ethanol followed by 6.00 g (0.26 g-atom) of sodium, and the reaction mixture stirred and heated until all the sodium had dissolved. The temperature of the reaction mixture was then raised to the reflux point, and a mixture of 29.04 g (0.20 mol) of 2,4-dimethylbenzyl cyanide and 64.88 g (0.30 mol) of diethyl 3,3-dimethyl glutarate added, dropwise, over a 2 hour period through the addition funnel. When the addition was complete, the reaction mixture was maintained at reflux for 12 hrs. At the end of this time, approximately ⅔ of the ethanol was distilled off, and the reaction mixture refluxed for 2 hrs. more, then cooled to room temperature and poured into 600 ml of an ice water mixture.

The basic aqueous solution was extracted twice with 300 ml of ether, and then acidified (ph=3) with 6N HCl. An oil formed, and the aqueous acid solution was extracted twice with 250 ml portions of ether. The ether phase from the extraction of the aqueous acid was washed twice with water, dried over anhydrous MgSo$_4$, and stripped to leave 52.83 g (84%) of ethyl 6-(2',4'-Dimethylphenyl)-6-cyano-5-keto-3,3-dimethylhexanoate as a clear, colorless, very viscous oil. This oil was not purified, but was characterized by infrared and nuclear magnetic resonance spectrometry.

IR (neat, μ principal absorptions): 2.8–3.2 (OH, enol); 4.55 (C≡N); 5.85, 6.02, 6.19 (C=O); 6.3 (C=C); 7.45, 8.25, 9.85, 12.25.

NMR (CDCl$_3$, σ): 1.20 (multiplet, 9H); 2.33 (multiplet, 8H); 2.68 (multiplet, 2H); 4.17 (quartet, 2H): 4.90 and 12.0 (singlet, 1H); 7.05 (multiplet, 3H).

EXAMPLE XVII

Preparation of 2-(2',4'-Dimethylphenyl)-5,5-dimethyl-1,3-cyclohexanedione and 6-(2',4'-Dimethylphenyl)-5-keto-3,3-dimethylhexanoic acid A one-neck round bottom flask was charged with 52.50 g (0.17 mol) of ethyl 6-(2',4'-dimethylphenyl)-6-cyano-3,3-dimethylhexanoate, 250 ml of concentrated hydrochloric acid, 250 ml of glacial acetic acid, and 100 ml of water. The reaction mixture was stirred and refluxed for 48 hours. After 12 hours and 24 hrs. of refluxing, an additional 100 ml of conc. HCl and 100 ml glacial HOAC were added. After 48 hours, the mixture was stripped to dryness under reduced pressure. To the residue were added 150 ml of water and 150 ml of ethyl ether, and the mixture shaken vigorously. A white, crystalline precipitate formed, and this was removed by suction filtration to give 13.20 g (32%) of 2-(2',4'-Dimethylphenyl)-5,5-dimethyl-1,3-cyclohexanedione as a white, crystalline solid, m.p. 167°–168.5° C.

Calcd. for C$_{16}$H$_{20}$O$_2$: C, 78.65; H, 8.25 Found: C, 78.68; H, 8.12

The ether layer was separated from the filtrate, washed once with water, dried over anhydrous MgSO$_4$ and stripped to give 29.04 g (65%) of 6-(2',4'-dimethylphenyl)-5-keto-3,3-dimethylhexanoic acid as a viscous yellow oil. This oil was not purified, but was characterized by infrared and nuclear magnetic resonance spectrometry.

IR (CHCl$_3$, μ principal absorptions): 2.9–4.3 (OH); 5.90 (C=O)

NMR (CDCl$_3$, σ): 1.10 (singlet, 6H); 2.20 (singlet, 3H); 2.30 (singlet, 3H); 2.50 (singlet, 2H); 2.62 singlet, 2H); 3.70 (singlet, 2H); 7.08 (singlet, broad, 3H).

EXAMPLE XVIII

Preparation of 2-(2'-Chlorophenyl)-1,3-cyclohexanedione

A 500 ml round bottom flask was charged with 10.0 g (0.0416 mol) of 6-(2'-chlorophenyl)-5-ketohexanoic acid and 100 ml of 72% sulfuric acid. The reaction mixture was stirred and heated to 120° C. for 5½ hours (oil bath), then poured into 600 ml of an ice water mixture. A tacky, white solid formed, and this was extracted into 300 ml of methylene chloride. The CH$_2$Cl$_2$ was washed six times with water, dried over anhydrous MgSO$_4$ and stripped to leave 8.87 g of a tacky, white solid. This material was recrystallized from ethyl acetate to give 5.85 g (63%) of 2-(2'-chlorophenyl)-1, 3-cyclohexanedione as a white, crystalline solid, m.p. 148.5°–149° C.

Calculated for: C$_{12}$H$_{11}$ClO$_2$: C, 64.73; H, 4.98 Found: C, 64.49; H, 4.89

EXAMPLE XIX

Preparation of 6-(2',4'-Dimethylphenyl)-5-ketohexanoic acid

Utilizing the procedure of EXAMPLE XVII ethyl 6-(2',4'-dimethylphenyl)-6-cyano-5-ketohexanoate was hydrolyzed in the presence of concentrated hydrochloric acid to prepare 6-(2',4'-dimethylphenyl)-5-ketohexanoic acid in 49% yield as a tan solid, m.p. 75.0°–76.5° C. This solid was characterized by infrared and nuclear magnetic resonance spectrometry.

(IR (CHCl$_3$, μ principal absorptions): 2.9–4.2 (OH); 5.92 C=O)

NMR (CDCl$_3$, σ): 1.7–3.3 (multiplet, 6H); 2.48 (singlet 3H); 3.71 (singlet, 2H); 7.31 (singlet, broad, 3H)

EXAMPLE XX

Preparation of Ethyl 6-(2',4'-Dimethylphenyl)-5-ketohexanoate

A 500 ml one-neck round bottom flask equipped with a Soxhlet extraction apparatus containing 100 g of molecular sieves having a pore size of 3A was charged with 12.74 g (0.0544 mol) of 6-(2',4'-dimethylphenyl)-5-ketohexanoic acid, 125 ml of absolute ethanol, 125 ml of dry benzene, and 2.0 ml of concentrated sulfuric acid. The mixture was refluxed for 12 hours, then ⅔ of the ethanolbenzene removed under reduced pressure. The residue was poured into 500 ml of ice water, and extracted into 300 ml of ether. The ether was washed three times with 10%, K$_2$CO$_3$, then once with water, dried over anhydrous MgSO$_4$, and removed to leave 13.34 g of a dark yellow oil. This was distilled to give 12.77 g (89%) of ethyl 6-(2',4'-Dimethylphenyl)-5-ketohexanoate as a clear, colorless oil, b.p. 133°–145° C. (0.05 mm). This oil was further characterized by infrared and nuclear magnetic resonance spectrometry.

IR (neat, μ principal absorptions): 5.85 (=O), 8.60 (C=O)

NMR (CDCl$_3$, σ): 1.15 (triplet, 3H); 1.50–2.6 (multiplet, 6H); 2.10 (singlet, 3H); 2.20 (singlet, 3H; 3.52 (singlet, 2H); 3.95 (quartet, 2H); 6.80 (singlet, broad, 3H).

EXAMPLE XXI

Preparation of 2-(2',4'-Dimethylphenyl)-1,3-cyclohexanedione

A 500 ml 3-neck round bottom flask was equipped with a mechanical stirrer, addition funnel, and reflux condenser. The glassware was dried thoroughly and the flask charged with 4.62 g (0.096 g-atoms) of 50% sodium hydride in mineral oil. The oil was washed off the NaH using toluene, and then 100 ml of toluene added. The mixture was warmed to 65° C. and 12.62 g (0.0481 mol) of ethyl 6-(2',4'-dimethylphenyl)-5-ketohexanoate added, dropwise, over a 2 hr. period. The mixture was maintained at 65° C. for 12 hrs., then carefully quenched with 25 ml of ice water. The reaction mixture was diluted with 250 ml of water and extracted twice with 150 ml of ether. The aqueous base solution was acidified to pH=3 with 6N HCl, and extracted twice with 150 ml of methylene chloride. The methylene chloride was washed with water, dried over anhydrous MgSO$_4$, and stripped to give 5.88 g of a semi-solid. This was recrystallized from ethyl acetate to give 5.10 g (49%) of 2-(2',4'-Dimethylphenyl)-1, 3-cyclohexanedione as a white, crystalline solid, m.p. 143°–145° C.

Calculated for: C$_{14}$H$_{16}$O$_2$: C, 77.75; H, 7.46 Found: C, 76.99; H, 7.46

EXAMPLE XXII

Preparation of Ethyl 6-(2',5'-Dimethylphenyl)-6-cyano-5-keto-3,3-dimethylhexanoate Utilizing the procedure of EXAMPLE XVI, 29.04 g (0.200 mol) of 2,5-dimethylbenzyl cyanide and 64.88 g (0.300 mol) of diethyl 3,3-dimethyl glutarate were reacted to yield 45.24 g (72%) of ethyl 6-(2', 5'-dimethylphenyl)-6-cyano -5-keto-3,3-dimethylhexanoate as a clear, colorless viscous oil. Structure was confirmed by infrared and nuclear magnetic resonance spectrometry.

IR (neat, μ principal absorptions): 2.9–3.7 (OH, enol); 4.55 (C=N); 5.80, 5.98, 6.10 (C=O); 6.23 (C=C); 7.35; 7.60; 8.15; 9.70; 12.30.

NMR (CDCl$_3$, σ): 1.18 (multiplet, 9H); 1.67–2.73 (multiplet, 10H); 4.12 (quartet, 2H); 4.88 (singlet 1H); 7.05 (broad, singlet, 3H).

EXAMPLE XXIII

Preparation of 6-(2',5'-Dimethylphenyl)-5-keto-3,3-dimethyl-hexanoic acid and 2-(2',5'-Dimethylphenyl)-5,5-dimethyl-1,3 cyclohexanedione A solution of 45.24 g (0.14 mol) of ethyl 6-(2', 5'-Dimethylphenyl)-6-cyano-5-keto-3, 3-dimethylhexanoate, 250 ml of glacial acetic acid. 250 ml of concentrated HCl, and 70 ml of water was refluxed for 48 hours. After 24 hours, an additional 100 ml of concenrated HCl and 150 ml of glacial acetic acid were added.

After 48 hours of refluxing, the reaction mixture was cooled to room temperature and the solvent removed under reduced pressure. The residue was shaken vigorously with 250 ml of water and 250 ml of diisopropyl ether. A white, crystalline precipitate formed which was removed by suction filtration to give 7.90 g (23% yield) of 2-(2'-, 5'-dimethylphenyl)-5, 5-dimethyl-1,3-cyclohexanedione m.p. 168°-170° C.

Calculated for $C_{16}H_{20}O_2$: C, 78.65; H, 8.25 Found: C, 78.16; H, 8.03

The ether layer was separated from the filtrate, washed once with water, dried over anhydrous $MgSO_4$, and stripped to give 17.97 g of 6-(2',5'-Dimethylphenyl)-5-keto-3,3-dimethyl hexanoic acid as a yellow oil. This oil was not purified, but was characterized by infrared and nuclear magnetic resonance spectrometry.

IR (neat, $\mu$, principal absorptions): 2.9-3.8 (OH); 5.90 (C=O); 12.3 (aromatic)

NMR ($CDCl_3$, $\sigma$): 1.08 (singlet, 6H); 2.03 (singlet, 2H); 2.13 (singlet, 2H); 2.27 (singlet, 3H); 2.33 (singlet, 3H); 7.0 (singlet, 3H)

EXAMPLE XXIV

Preparation of Ethyl 6-(2',5'-dimethylphenyl)-5-keto-3,3-dimethylhexanoate

Utilizing the procedure of EXAMPLE XX 6-(2',5'-dimethylphenyl)-5-keto-3,3-dimethyl hexanoic acid was esterified with absolute ethanol in the presence of a catalytic amount of concentrated sulfuric acid to provide 15.52 g (78% yield) of ethyl 6-(2',5'-dimethylphenyl)-5-keto-3,3-dimethylhexanoate as a pale viscous oil.

EXAMPLE XXV

Preparation of 2-(2',5'-Dimethylphenyl)-5,5-dimethyl-1,3-cyclohexanedione

Utilizing the procedure of EXAMPLE XXI, 6-(2',5'-dimethylphenyl-5-keto-3, 3-dimethylhexanoate was treated with sodium hydride to yield 9.87 of crude product, which on recrystallization yielded 8.77 g (64%) of 2-(2',5'-dimethylphenyl)-5,5-dimethyl-1, 3-cyclohexanedione as a white, crystalline solid m.p. 167°-168° C.

Selected 2-aryl-1, 3-cyclohexanedione compounds, representative of those useful in accordance with this invention were tested with respect to their miticidal, mite ovicidal and pre-emergent and post-emergent herbicidal activity.

Suspensions of the test compounds were prepared by dissolving one gram of compound in 50 milliliters of acetone in which had been dissolved 0.1 gram (10 percent of the weight of compound) of an alkylphenoxyethanol surfactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described hereinbelow were obtained by diluting the stock suspension with water. The test procedures were as follows:

MITE FOLIAGE SPRAY TEST

Adults and nymphal stages of the two-spotted mite (*tetranychus urticae* (Koch)), reared on Tendergreen bean plants at 80°±5° F. and 50±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psi. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80°±5° F. and 50±5 percent relative humidity for four days, after which, a mortality count of motile forms was made on the leaves of the test plants. Any individual which was capable of locomotion upon prodding was considered living.

MITE OVICIDE TEST

The test organism was the egg of the two-spotted mite (*Tetranychus urticae* (Koch)), as obtained from adults reared on Tendergreen bean plants under controlled conditions of 80°±5° F. and 50±5 percent relative humidity. Heavily infested leaves from a stock culture were placed on the primary leaves of two bean plants six to eight inches in height, growing in a two-and-a-half inch clay pot. Females were allowed to oviposit for a period of 48 hours and then the leaves of the infested plants were dipped in a solution containing 800 parts of tetraethyl pyrophosphate per million parts of water in oder to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The potted plants (one pot per compound) were placed on a revolving turntable and sprayed with 100-110 milliliters of test compound formulation by use of a DeVilbis spray gun set at 40 psig. air pressure. This application which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80°±5° F. and 50±5 percent relative humidity for four days, after which a microscopic examination was made of unhatched (dead) and hatched (living) eggs.

In these tests the pesticidal activity of the compounds against mites and mite eggs were rated as follows:
A=Excellent Control
B=Partial Control
C=No Control

PRELIMINARY HERBICIDE SEED GERMINATION TEST

The following seeds were used in this test:

| | |
|---|---|
| Perennial rye grass | *Solium perenne* |
| Crabgrass | *Digitaria sanguinalis* |
| Red root pigweed | *Amaranthus retroflexus* |
| Mustard | *Brassica pincea* var. *foliosa* (Florida broadleaf) |

Two seed-oil mixtures were prepared as follows:

| | |
|---|---|
| Mixture I | 196 cc. Rye grass seed |
| | 75 cc. Mustard seed |
| | 18,000 cc. Sifted, fairly dry soil |
| Mixture II | 99 cc. Crabgrass seed |
| | 33 cc. Amaranthus |
| | 18,000 cc. Sifted, fairly dry soil |

Each of the above mixtures was rolled separately in 5 gallon containers for approximately one-half hour on ball mill to insure uniform mixing of seeds and soil. For each compound four 3-inch pots were filled with soil to within 1½ inches of top of pots. To 2 of these pots were added 70 cc. of Mixture I. To the remaining 2 pots were added 70 cc. of Mixture II. The seed-soil mixture was tamped firmly, and the pots were removed to the greenhouse and watered lightly. About 2 hours after planting, 25 milliliters of the test formulation were added to each of 2 pots for each soil-seed mixture; i.e., one replicate of each seed mixture per concentration. An equal volume of a water solution containing acetone and an emulsifier in the same concentration as the herbicidal mixture but without the candidate herbicide was also added to each of the soil-seed mixtures. These pots were used as check or control units. The test compounds were formulated by standard procedure of dissolving in acetone, addition of an emulsifier, and dilution with water. Tests were conducted on all compositions at low concentration (100 ppm.). Certain compositions were also tested at high concentration (1000 ppm). The pots were held in the greenhouse and watered lightly until results were taken. Ten to twelve days after application of chemical, injury was noted for each species by comparing treated vs. untreated pots. Ratings were made at both the high and low concentrations (1000 ppm and 100 ppm) according to the following designations:

5 = no seedlings emerged
4 = few seedlings emerged and/or very severe stunting
3 = moderate reduction in stand and/or moderate stunting.
2 = very slight reduction in stand and/or slight stunting
1 = no injury; seedlings appear no different with respect to stand or growth than untreated controls

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below.

TABLE I

PHYSICAL PROPERTIES AND BIOLOGICAL ACTIVITY OF 2-ARYL-1,3-CYCLOHEXANEDIONE COMPOUNDS AND THEIR ALKALI METAL SALTS

| | | | | | | | | | Miticidal | | Post-Emergent Herbicidal | | | | | | Pre-Emergent Herbicidal | | |
|---|---|---|---|---|---|---|---|---|---|---|---|---|---|---|---|---|---|---|---|
| $R_1$ | $Z''$ | $R_5$ | $R_6$ | $Z'$ | $Z'''$ | $Y$ | MP °C. | | Adult | Egg | Bean | Corn | Tomato | Cotton | Soybean | Rye | Crab-grass | Amaranthus | Mustard |
| Cl | H | H | H | H | H | H | 148.5–149 | | A | A | 2 | 4 | 1 | 2 | 2 | 5 | 5 | 1 | 2 |
| Cl | H | H | H | Cl | H | H | 163–165 | | A | A | 2 | 3 | 2 | 2 | 2 | 5 | 5 | 3 | 3 |
| —CH$_3$ | H | H | H | H | H | H | 146–147 | | B | C | 2 | 4 | 1 | 2 | 2 | 5 | 4 | 2 | 3 |
| —CH$_3$ | H | —CH$_3$ | —CH$_3$ | H | H | H | 143.5–145 | | A | A | 2 | 3 | 2 | 2 | 1 | 5 | 5 | 1 | 2 |
| —CH$_3$ | H | —CH$_3$ | —CH$_3$ | —CH$_3$ | H | H | 178–179.5 | | A | A | 1 | 1 | 1 | 2 | 1 | 5 | 5 | 1 | 3 |
| —CH$_3$ | H | —CH$_3$ | —CH$_3$ | H | —CH$_3$ | H | 167–168.5 | | A | A | 2 | 2 | 2 | 2 | 1 | 5 | 5 | 4 | 4 |
| —CH$_3$ | H | —CH$_3$ | —CH$_3$ | —CH$_3$ | Cl | H | 168–169 | | A | A | 1 | 1 | 2 | 2 | 1 | 5 | 5 | 3 | 3 |
| Cl | H | —CH$_3$ | —CH$_3$ | H | H | Na+ | 238–240 | | C | B | 1 | 1 | 1 | 1 | 1 | 1 | 1 | 1 | 1 |
| Cl | H | H | H | H | H | Na+ | >250 | | A | A | 3 | 4 | 2 | 2 | 2 | 5 | 5 | 4 | 4 |
| Cl | H | —CH$_3$ | —CH$_3$ | —CH$_3$ | H | Na+ | >250 | | B | B | 1 | 5 | 1 | 2 | 2 | 5 | 5 | 3 | 3 |
| —CH$_3$ | H | —CH$_3$ | —CH$_3$ | Cl | H | Na+ | >250 | | A | A | 2 | 4 | 2 | 2 | 2 | 5 | 5 | 3 | 5 |
| —CF$_3$ | H | —CH$_3$ | —CH$_3$ | NO$_2$ | H | H | 235–237 | | C | C | 2 | 1 | 1 | 1 | 1 | 1 | 1 | 1 | 1 |
| —CF$_3$ | H | —CH$_3$ | —CH$_3$ | H | H | H | 209–211.5 | | B | C | 1 | 1 | 1 | 3 | 1 | 4 | 3 | 3 | 2 |
| —CF$_3$ | H | —CH$_3$ | —CH$_3$ | Cl | H | H | 209.5–211 | | A | B | 1 | 1 | 1 | 1 | 1 | 5 | 4 | 3 | 2 |
| Cl | H | —CH$_3$ | —CH$_3$ | NO$_2$ | H | H | 240–245 | | C | C | 1 | 1 | 1 | 1 | 1 | 1 | 1 | 1 | 1 |
| Cl | —NO$_2$ | —CH$_3$ | —CH$_3$ | NO$_2$ | H | H | 233–235 | | A | B | 2 | 1 | 1 | 1 | 2 | 1 | 3 | 1 | 2 |
| Cl | —NO$_2$ | —CH$_3$ | —CH$_3$ | H | H | H | 226–229 | | C | C | 2 | 1 | 1 | 1 | 1 | 4 | 3 | 1 | 2 |
| —CN | —NO$_2$ | —CH$_3$ | —CH$_3$ | —NO$_2$ | H | H | 234d | | A | C | 1 | 1 | 1 | 1 | 1 | 1 | 1 | 1 | 1 |
| Cl | H | —CH$_3$ | —CH$_3$ | —NO$_2$ | H | H | 238d | | C | C | 2 | 2 | 2 | 1 | 2 | 1 | 1 | 1 | 2 |
| Cl | H | —CH$_3$ | —CH$_3$ | —CH$_3$ | H | H | 248–251 | | B | C | 2 | 2 | 1 | 2 | 3 | 5 | 5 | 3 | 3 |
| Cl | H | —CH$_3$ | —CH$_3$ | Cl | H | H | 141–142 | | A | A | 1 | 2 | 2 | 2 | 2 | 5 | 5 | 3 | 4 |
| Cl | H | —CH$_3$ | —CH$_3$ | —NO$_2$ | H | H | 207–209 | | A | A | 1 | 1 | 1 | 1 | 1 | 5 | 5 | 3 | 3 |
| Cl | Cl | —CH$_3$ | —CH$_3$ | Cl | H | H | 288–290 | | C | A | 3 | 3 | 1 | 3 | 2 | 5 | 5 | 3 | 1 |
| Cl | Cl | —CH$_3$ | —CH$_3$ | H | H | H | 227–229 | | A | A | 1 | 4 | 2 | 1 | 1 | 5 | 5 | 1 | 3 |
| —CH$_3$ | —CH$_3$ | —CH$_3$ | —CH$_3$ | —CH$_3$ | H | H | 196–198 | | A | A | 1 | 2 | 1 | 2 | 2 | 5 | 5 | 2 | 2 |
| —CH$_3$ | —CH$_3$ | —CH$_3$ | —CH$_3$ | —CH$_3$ | H | H | 212–216 | | A | A | 1 | 1 | 2 | 1 | 1 | 5 | 5 | 1 | 3 |
| —CH$_2$CH$_3$ | H | H | —CH$_3$ | —CH$_3$ | H | H | 177–186 | | A | A | 1 | 2 | 2 | 1 | 2 | 5 | 5 | 3 | 2 |
| —CH$_3$ | —CH$_3$ | (cyclohexyl) | —CH$_3$ | H | H | H | 118–121 | | C | C | 1 | 1 | 1 | 1 | 2 | 5 | 5 | 1 | 1 |
| —CH$_3$ | H | —CH$_3$ | —CH$_3$ | —CH$_3$ | H | H | 196–202 | | C | C | 2 | 3 | 2 | 2 | 1 | 5 | 5 | 2 | 3 |
| —CH$_3$ | H | —CH$_3$ | —CH$_3$ | —Cl | H | H | 190–192 | | A | B | 1 | 1 | 1 | 1 | 1 | 5 | 5 | 3 | 3 |
| —CH$_3$ | Cl | —CH$_3$ | —CH$_3$ | H | H | H | 188–191 | | C | A | 1 | 1 | 1 | 2 | 1 | 5 | 4 | 3 | 3 |
| —CH$_3$ | —CH$_3$ | —CH$_3$ | —C$_6$H$_5$ | —CH$_3$ | H | H | 215–216 | | C | C | 1 | 1 | 1 | 1 | 1 | 5 | 5 | 4 | 3 |
| —CH(CH$_3$)$_2$ | —CH$_3$ | —CH$_3$ | —CH$_3$ | C(CH$_3$)$_3$ | H | H | 244–249 | | C | C | 1 | 2 | 2 | 2 | 2 | 1 | 1 | 1 | 1 |
| —OCH$_3$ | H | —CH$_3$ | CH$_3$ | H | H | H | 161–164 | | C | C | 1 | 3 | 1 | 1 | 2 | 5 | 5 | 2 | 3 |
| —CH$_3$ | H | —CH$_3$ | CH$_3$ | —CH$_3$ | H | H | 115–119 | | C | C | 2 | 3 | 2 | 2 | 1 | 5 | 5 | 1 | 2 |

TABLE I-continued

PHYSICAL PROPERTIES AND BIOLOGICAL ACTIVITY OF 2-ARYL-1,3-CYCLOHEXANEDIONE COMPOUNDS AND THEIR ALKALI METAL SALTS

| | | | | | | | MP | Miticidal | | Post-Emergent Herbicidal | | | | | Pre-Emergent Herbicidal | | |
|---|---|---|---|---|---|---|---|---|---|---|---|---|---|---|---|---|---|
| $R_1$ | $Z'''$ | $R_5$ | $R_6$ | $Z'$ | $Z''$ | Y | °C. | Adult | Egg | Bean | Corn | Tomato | Cotton | Soybean | Rye | Crab-grass | Amar-anthus | Mustard |
| —$CH_3$ | —$OCH_3$ | —$CH_3$ | —$CH_3$ | H | H | H | 172–174 | A | B | 1 | 2 | 1 | 1 | 1 | 5 | 5 | 1 | 3 |
| —$CH_3$ | —$OCH_3$ | —$CH_3$ | —$CH_3$ | —$CH_3$ | H | H | 155–159 | A | A | 1 | 5 | 1 | 2 | 2 | 1 | 1 | 1 | 1 |
| —$CH_3$ | —$CH_3$ | —$CH_3$ | —$CH_3$ | —$OCH_3$ | H | H | 155–159 }$^a$ | A | A | 1 | 5 | 1 | 2 | 2 | 1 | 1 | 1 | 1 |
| —$CH_3$ | H | —$CH_3$ | —$CH_3$ | H | H | H | 143–145 | A | A | 1 | 1 | 1 | 1 | 1 | 5 | 5 | 2 | 3 |
| —$CH_3$ | H | ⬡ | | —$CN$ | H | H | 188–191 | A | C | 2 | 1 | 1 | 2 | 1 | 1 | 1 | 1 | 1 |
| —$CH_3$ | —$CN$ | —$CH_3$ | —$CH_3$ | H | H | H | 193–195 | A | C | 2 | 2 | 2 | 2 | 1 | 1 | 1 | 1 | 1 |

$^a$ a mixture of the two isomers

It will be understood that the plant species employed in the above tests are merely representative of a wide variety of plant pest that can be controlled by the use of the compounds of this invention. The compounds contemplated in this invention may be applied as mite ovicides, miticides and pre-emergent herbicides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristic for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. When used as herbicides they may be used in the soil or directly upon the seeds to be treated. It will be appreciated that the compounds of this invention can also be used in combination with other biologically active compounds.

What is claimed is:

1. A method of preparing a compound of the formula:

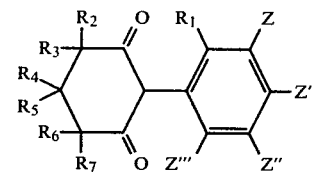

which comprises reacting a compound of the formula:

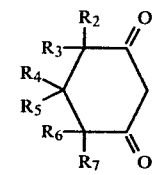

with a compound of the formula:

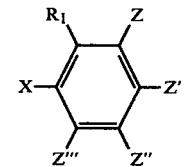

in the presence of base, wherein:

X is fluorine or chlorine;

Z, Z" and Z'" are individually hydrogen, polyhaloalkyl, halogen, cyano, nitro, alkyl, alkoxy, alkylthio, alkylsulfinyl, alkylsulfonyl, alkanoyl, amido, amino or haloalkyl;

Z' is nitro or alkylsulfonyl or Z' is alkyl or alkoxy when either Z'" or R₁ is nitro;

R₁ is alkyl, haloalkyl, halogen, or polyhaloalkyl;

R₂, R₃, R₄, R₅, R₆, R₇ are individually hydrogen or either substituted or unsubstituted alkyl or phenyl wherein the permissible substituents are one or more alkyl, cyano, halogen, nitro, alkoxy, alkylthio, alkylsulfinyl, alkylsulfonyl or dialkylamino substituents or any two R₂, R₃, R₄, R₅, R₆ or R₇ substituents together may form an alkylene or alkenylene chain having from 2 to 20 carbon atoms completing a 3, 4, 5, 6 or 7 membered ring structure;

with the proviso that R₁, R₂, R₃, R₄, R₅, R₆, R₇, Z, Z', Z" and Z'" substituents individually may not include more than ten aliphatic carbon atoms.

* * * * *